(12) United States Patent
Bartels et al.

(10) Patent No.: US 8,712,543 B2
(45) Date of Patent: Apr. 29, 2014

(54) IMPLANTABLE DEVICE

(75) Inventors: Klaus Bartels, Berlin (DE); Timo Frenzel, Berlin (DE); Stefan Knorr, Berlin (DE); Gernot Kolberg, Berlin (DE); Michelle Maxfield, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 13/433,269

(22) Filed: Mar. 28, 2012

(65) Prior Publication Data
US 2012/0253441 A1    Oct. 4, 2012

Related U.S. Application Data

(60) Provisional application No. 61/469,107, filed on Mar. 30, 2011.

(51) Int. Cl.
| A61N 1/00 | (2006.01) |
| A61N 1/16 | (2006.01) |
| A61N 1/375 | (2006.01) |
| A61N 1/05 | (2006.01) |
| A61N 1/37 | (2006.01) |
| A61N 1/08 | (2006.01) |
| A61N 1/18 | (2006.01) |

(52) U.S. Cl.
USPC ............................................ 607/116; 607/63

(58) Field of Classification Search
USPC ........................................................ 607/116
See application file for complete search history.

(56) References Cited

U.S. PATENT DOCUMENTS

| 2006/0200218 A1* | 9/2006 | Wahlstrand | 607/116 |
| 2008/0071338 A1* | 3/2008 | Jiang et al. | 607/119 |
| 2008/0262584 A1* | 10/2008 | Bottomley et al. | 607/119 |
| 2009/0149933 A1* | 6/2009 | Ameri | 607/119 |
| 2009/0171336 A1* | 7/2009 | Weber | 606/27 |
| 2009/0234368 A1 | 9/2009 | Gore | |
| 2010/0174348 A1* | 7/2010 | Bulkes et al. | 607/116 |
| 2010/0208397 A1 | 8/2010 | Johnson | |

FOREIGN PATENT DOCUMENTS

WO    2006/105066    10/2006

OTHER PUBLICATIONS

European Search Report dated Aug. 6, 2013, 6 pages.

* cited by examiner

*Primary Examiner* — Carl H Layno
*Assistant Examiner* — Erin Piateski
(74) *Attorney, Agent, or Firm* — ARC IP Law, PC; Joseph J. Mayo

(57) ABSTRACT

A device that can be temporarily introduced in a body or permanently implanted in a body comprising at least one elongated electric function conductor for transmitting treatment signals or diagnostic signals, or both, and further comprising a connector, which is connected to the function conductor and disposed on a proximal end of the function conductor, for connecting the device to a further device. Characteristic impedance is present between the function conductor and at least one further conductor. A transition region from the function conductor to the connector is designed such that a characteristic impedance between the function conductor and the further conductor in the transition region is designed to be between the corresponding characteristic impedance of the device in a line section distal of the transition region and the characteristic impedance present proximal of the transition region when the connector is connected to a further device.

18 Claims, 11 Drawing Sheets

IMPLANTABLE DEVICE

This application claims the benefit of U.S. Provisional Patent Application 61/469,107, filed on 30 Mar. 2011, the specification of which is hereby incorporated herein by reference.

BACKGROUND OF THE INVENTION

1. Field of the Invention

Embodiments of the invention relate to a permanently or temporarily implantable device comprising an elongated electric conductor.

2. Description of the Related Art

Such devices, for example electrode lines for electrostimulation and/or for picking up electronic signals, have the disadvantage that the electric conductor thereof may heat up in a nuclear magnetic resonance tomograph (also referred to as magnetic resonance imaging scanner) because the alternating magnetic fields present in the nuclear magnetic resonance tomograph induce quite significant electric currents in the electric conductor. Such induced currents can also be delivered to surrounding tissue by electrode poles of the electrode line and thus result in undesirable heating of tissue, for example. This heating may lastingly damage the body tissue and should be kept to a minimum. In comparison with conventional implants, the heating is to be reduced. For this reason, cardiac pacemaker patients today generally cannot be examined in a nuclear magnetic resonance tomograph, or only to a limited extent.

Typically, implantable cardiac pacemakers or defibrillators (hereinafter jointly referred to as cardiac stimulators or implantable pulse generators (IPG)) are connected at least to a stimulation electrode line that comprises a standardized electrical connection at the proximal end thereof provided for connection to the cardiac pacemaker or defibrillator, and that comprises one or more electrode poles at the distal end thereof provided for placement in the heart. Such an electrode pole is used to deliver electric pulses to the tissue (myocardium) of the heart or to sense electric fields, so as to be able to sense an activity of a heart as part of the sensing process. For these purposes, electrode poles typically form electrically conductive surface sections of an electrode line. Electrode poles are typically provided as annular electrodes in the form of a ring around the electrode line, or in the form of tip electrodes, at the distal end of the electrode line. The electrode poles are electrically conductively connected to contacts of the electric connection of the electrode line at the proximal end by way of one or more electric conductors. In this way, one or more electric conductors, which electrically connect one or more of the electrode poles to one or more of the contacts, run between the contacts of the electric connection of the electrode lines at the proximal end and the electrode poles at the distal end of the electrode line. These electric conductors can be used both to transmit stimulation pulses to the electrode poles and to transmit electric signals picked up by the electrode poles to the proximal end of the electrode line and will also be referred to as function lines hereinafter in the description. Such function lines are electric conductors that are required for the functions of the respective electrode line, and as such they are exposed to the risk that electric currents are induced in them by external alternating magnetic fields, which can lead, for example, to undesirable heating of the function lines or of the electrode poles connected thereto, or can lead to the delivery of currents to the surrounding tissue by way of the electrode poles, and thereby to heating of the surrounding tissue.

BRIEF SUMMARY OF THE INVENTION

Embodiments of the invention enable a device that reduces heating resulting from energy applied by a nuclear magnetic resonance tomograph, and hence heating on the contact surfaces with the surrounding tissue.

Accordingly this feature is achieved by a device that can be temporarily introduced in a body or permanently implanted in a body, comprising at least one elongated electric function conductor for transmitting treatment signals or diagnostic signals, or both, and further comprising a connector, which is connected to the function conductor and disposed on a proximal end of the function conductor, for connecting the device to a further device, with a characteristic line impedance being present between the function conductor and at least one further conductor, characterized in that a transition region from the function conductor to the connector is designed such that a characteristic impedance between the function conductor and the further conductor in the transition region is designed to be between the corresponding characteristic impedance of the device in a line section located distal of the transition region and the characteristic impedance that is present proximal to the transition region when the connector is connected to a further device. The term "characteristic impedance" includes both ohmic resistance and frequency-dependent impedance.

In other words, embodiments of the invention are related to an elongated implant, which is used to stimulate and send signals to nerves, the brain, heart, and other organs, or to feed implantable sensors, comprising at least one feed line, which connects a proximal device to a distal electrode, wherein in the connector region the geometric and electric conditions are changed, without interfering with the therapeutic function. This change causes the characteristic resistance between the inner and outer conductors to change for electromagnetic waves that are coupled in.

In longitudinally homogeneous lines, such as cables or single wire assemblies, which are composed of at least two electric conductors, the characteristic impedance describes the ratio of current and voltage waves propagating in a common direction in relation to each other.

The implantable medical device is preferably an electrode line for connecting to an implantable medical device, wherein the electrode line comprises a connector at the proximal end and at least one electrode pole at the distal end, which is electrically connected to the connector by way of the at least one function conductor.

The transition region of the device is preferably provided with a filling, which influences the characteristic impedance and the properties and form of which are selected such that the desired characteristic impedance is obtained in the transition region.

The transition region preferably has a coaxial design.

It is particularly preferred for the filling to contain a material that acts dissipatively at least in an operating frequency range of magnetic resonance tomographs. Such a filling has the effect that waves induced by the magnetic resonance tomograph (and hence currents) are attenuated. This results in heating of the transition region, whereby tissue heating in the region of a distal end of the device, or tissue heating of the electrode line is prevented. When the transition region has a dissipative design, this means, in relation to the characteristic impedance, that the imaginary part thereof is greater than in a less dissipative transition region.

For insulating the connector region, the material of the filling is preferably selected so as to meaningfully change the characteristic impedance, which is to say within the meaning of a desired characteristic impedance. Based on this change, the reflection and transmission factors may take on a range between $R_{S,W}[0;1]$ and $T_{S,W}[-1,1]$.

The factor is dependent on the difference of the characteristic impedances between the connector $Z_S$ and the coil region $Z_W$.

$$R_{S,W} = \frac{Z_S - Z_W}{Z_S + Z_W} \text{ or } T_{S,W} = \frac{2Z_S}{Z_S + Z_W}$$

The individual impedances can be adjusted by way of the material and geometric properties. Assuming that the connector represents a coaxial system, the following characteristic impedance can be expected in the connector range at 64 MHz:

$$|Z|_{Stecker} = \sqrt{\frac{\mu}{\varepsilon_e}} \frac{1}{2\pi} \ln\left(\frac{D_{OC}}{D_{IC}}\right) = \frac{120\pi\Omega}{\sqrt{3} \cdot 2\pi} \cdot 0.606 = 20\Omega$$

For coiled regions, the characteristic impedance is considerably higher because of the inductance and capacitance per unit length. Here, $|Z|_{Wendel} \approx 150\Omega$ was determined metrologically. For an implantable generator (cardiac pacemaker, cardioverter/defibrillator, neurostimulator etc.), very low impedance of $|Z|_{Generator} = 2\text{-}10\Omega$ must be assumed because of the input circuit.

The characteristic impedances apply to line regions in which the geometric and electromagnetic properties remain constant. A continuous change of the characteristic impedance can be achieved when the geometric properties change over the run length. In addition, the electromagnetic properties can also vary. In terms of line theory, this creates a network composed of characteristic impedances that are connected in parallel.

The goal is to adjust the characteristic impedances by way of the geometric and electric properties such that a continuous transition develops from $|Z|_{Wendel}$ to $|Z|_{Generator}$. This can be achieved by using suitable materials, an adjusted diameter ratio, and by the transition from coaxial coils to coaxial tubes. The latter have significantly lower inductance per unit length. For $D_{OC} = 2.2$ mm and $D_{IC} = 0.1$ mm and relative permittivity $\varepsilon_r = 2$, this means:

$$|Z|_{Stecker} = \sqrt{\frac{\mu}{\varepsilon_e}} \frac{1}{2\pi} \ln\left(\frac{D_{OC}}{D_{IC}}\right) = \frac{120\pi\Omega}{\sqrt{2} \cdot 2\pi} \cdot 3.1 = 131\Omega$$

The diameter ratios can be optimized by varying the inductance per unit length of the coil. Because the wave propagation is additionally influenced by the conductivity or polarization losses of the insulating material, the amplitude of the propagating wave is attenuated over the length of the line. Reflections on interfaces due to non-adapted line elements thus have a lesser effect.

If the transition is to be designed to be low-reflecting and dissipative in the transition region to the connector, it is recommended to set the characteristic impedance similarly high. Taking the fact that the coaxial geometry does not change into consideration, this is preferably done by way of the material properties of the filling.

In addition to the characteristic impedance, the propagation constant in the waveguide influences the wave. This constant is dependent on the electromagnetic parameters and can be expressed as follows:

$$\gamma = \omega\sqrt{\mu_e \varepsilon_e} = \omega\sqrt{\mu_e\left(\varepsilon_0 R(\varepsilon_r) + j\left(\varepsilon_0 \Im(\varepsilon_r) + \frac{\sigma}{\omega\varepsilon_0}\right)\right)} = \alpha + j\beta$$

($\gamma$=propagation constant; $\alpha$=attenuation constant; $\beta$=phase constant)

Imaginary parts of the effective permittivity $\varepsilon_e$ as well as the conductivity are included in the attenuation constant; the effect of polarization losses is further increased by an elevated phase constant, because this constant has a prorated effect on each wave path.

For silicone, the propagation constant is:

$$\gamma_{Silikon} = j\omega\sqrt{\mu_e \varepsilon_e} = j\omega\sqrt{\mu_0 \varepsilon_0 \varepsilon_r} = 0 + 2.2j$$

For Plexiglas or silicone doped with higher conductivity ($\sigma$=0.1$\Omega$), the propagation constants are dissipative and more advantageous for the present case (f=64 MHz):

$$\gamma_{Plexiglass} = j\omega\sqrt{\mu_e \varepsilon_e} = 0.05 + 2.49j \text{ or } \gamma_{Silikon,dotiert} = j\omega\sqrt{\mu_e \varepsilon_e} = 4.9 + 5.2j$$

The impedance of the filling is preferably adapted to the characteristic impedance. The impedance adaptation is preferably caused by the material of the filling. Preferred materials for the filling are pyrolytic materials, doped plastic materials containing paraelectric, ferroelectric, diamagnetic, ferromagnetic, paramagnetic particles, and plastic materials with dielectric losses.

Fluoroplastics (PTFE, Teflon) and thermoplastic polycondensates (PEEK, PEK) are suitable materials for the filling in the transition region, having a doping made of the following metals:

platinum & titanium refractory materials: niobium, tantalum, palladium, tungsten The impedance of the filling is preferably lossy, so that the filling acts dissipatively.

The dissipation is preferably adjusted by means of the loss (such as conductivity) of the material of the filling.

The following table provides the conductivity of the materials:

| Pos. | Material | Conductivity in S/m | Source |
|---|---|---|---|
| 1. | Silver | $6.1 \cdot 10^6$ | [1] |
| 2. | Copper | $5.76 \cdot 10^6$ | [1] |
| 3. | Gold | $4.1 \cdot 10^6$ | [1] |
| 4. | Niobium | $\cdot 10^6$ | [2] |
| 5. | Tantalum | $0.69 \cdot 10^6$ | [1] |
| 6. | Palladium | $5.76 \cdot 10^6$ | [1] |
| 7. | Tungsten | $1.83 \cdot 10^6$ | [1] |
| 8. | Stainless steel | $0.115 \cdot 10^6$ | [1] |
| 9. | Platinum | $0.979 \cdot 10^6$ | [1] |
| 10. | Titanium | $0.207 \cdot 10^6$ | [1] |

[1]: White, Don: A Handbook on Electromagnetic Shielding Materials and Performance, Don White Consultants, Inc.; 2 edition (June 1980), ISBN 978-0932263087
[2]: Harry H. Binder: Lexikon der chemischen Elemente - das Periodensystem in Fakten, Zahlen und Daten (Encyclopedia of chemical elements - facts, numbers and data of the periodic table). Hirzel, Stuttgart 1999, ISBN 3-7776-0736-3

If the diameter ratio is small, preferably a smaller permittivity of the insulating material of the filling should be selected. For dissipative behavior, the material of the filling should be a (poorly conductive) material, with the characteristic impedance changing as little as possible.

The attenuation constant α, in contrast, should be as high as possible:

$$\alpha_S = \frac{\omega}{\sqrt{2}}\sqrt{|\varepsilon_e \mu| - \mathrm{Re}(\varepsilon_e \mu)}$$

wherein the conductivity is included in the complex-valued and effective permittivity $\in_e$:

$$\underline{\in}_e = \in_e' - j \in_e''$$

with $\in_e' = \in'$ and $$\varepsilon_e'' = \varepsilon'' \frac{\sigma_s}{\omega}$$

The filling is preferably disposed between an inner conductor and an outer conductor.

The filling is preferably designed so that the impedance thereof changes in the longitudinal direction of the transition region, for example in that the geometry of the filling changes in the longitudinal direction of the transition region.

It is further preferred for the impedance to have an adapted wave number, high reflection quality and/or high transmission quality.

The function conductor is, or the function conductors are, preferably designed as coils and form one or more inner and outer conductors of an electrode line, for example.

As an alternative, the function conductor or conductors can be designed as parallel wires and, for example, can likewise form the inner and outer conductors of an electrode line. Such inner and outer conductors can also be designed as a combination composed of a coil and parallel wires.

In all cases, the turn density of the coils may be constant.

In order to bring about characteristic impedance that varies substantially continuously, the turn density of the coils can change in the longitudinal direction of the transition region, and optionally beyond that.

In addition to the function conductors, optionally coil-shaped additional conductors can also be provided, which are not used, or which are not only used, for signal transmission, and therefore have a therapeutic function, but which minimize the coupling of electromagnetic waves on the function conductor or conductors.

BRIEF DESCRIPTION OF THE DRAWINGS

The invention will now be described in more detail based on embodiments with reference to the figures. In the drawings.

DETAILED DESCRIPTION OF THE INVENTION

Figure 1:
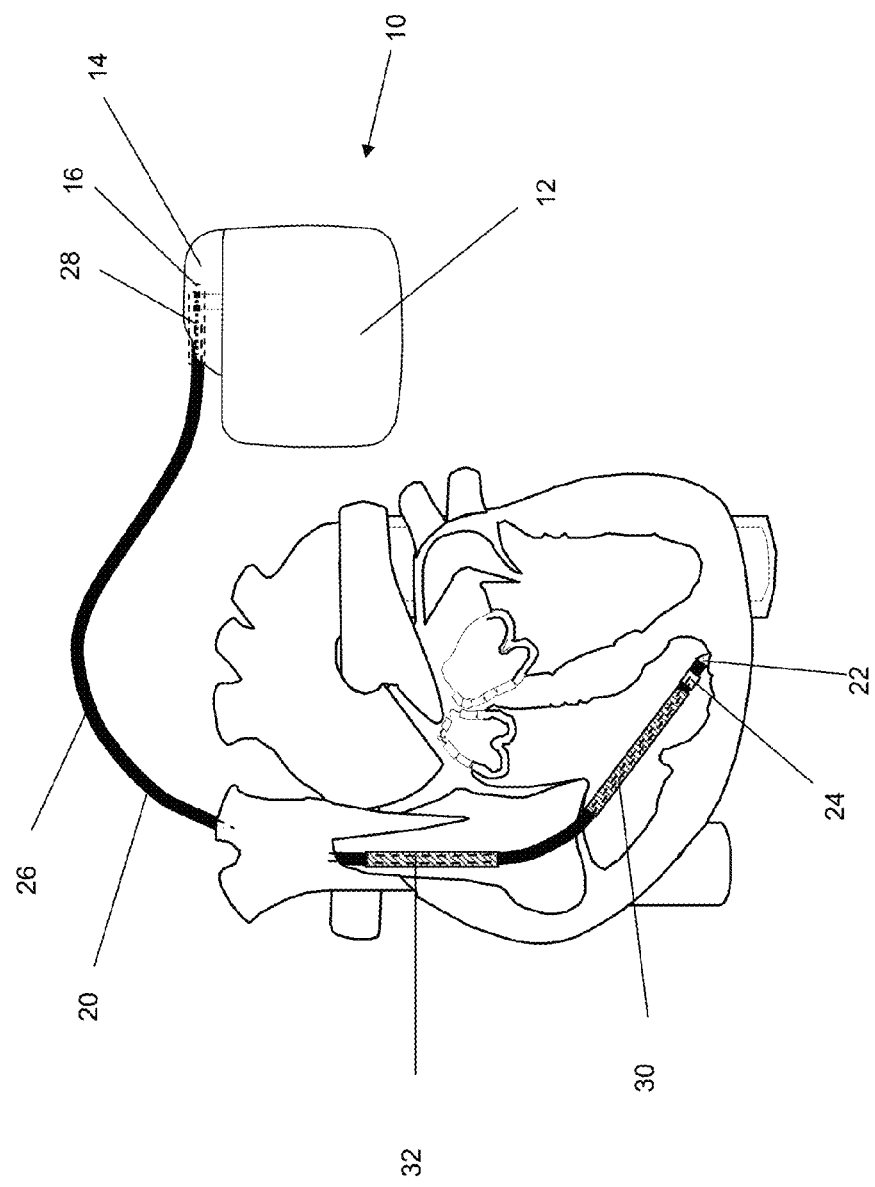
FIG. 1 shows an implantable cardiac stimulator 10 and an implantable electrode line 20 connected thereto as implantable medical devices.

FIG. 1 shows an implantable medical device in the form of an electrode line 20, comprising an elongated conductor and being connected to a further implantable medical device, which is to say an implantable cardiac stimulator 10.

The implantable cardiac stimulator 10 can be a cardiac pacemaker or a cardioverter/defibrillator (ICD). In the embodiment shown in FIG. 1, the cardiac stimulator 10 is a ventricular cardiac pacemaker and defibrillator. Other known cardiac stimulators are dual-chamber cardiac pacemakers for stimulating the right atrium and right ventricle, or biventricular cardiac pacemakers, which in addition to the right ventricle can also stimulate the left ventricle.

Such stimulators typically comprise a housing 12, which is generally made of metal and is therefore electrically conductive and can be used as a large-surface-area electrode pole. Typically, a terminal housing 14, which is also referred to as a header, is fastened to the outside of the housing 12. Such a header typically comprises contact bushings for receiving plug contacts. The contact bushings comprise electric contacts 16, which are connected to an electronics unit disposed in the housing 12 of the cardiac pacemaker 10 by way of corresponding conductors.

The electrode line 20 as defined by one or more embodiments of the invention constitutes an implantable medical device having an elongated electric function conductor. Electrode poles in the form of a tip electrode 22 and an annular electrode 24 disposed in the vicinity of the tip electrode are disposed at a distal end of the electrode line 20 in the manner known per se. The electrode poles 22 and 24 are designed to be used, depending on the function of a cardiac stimulator to which the electrode line 20 is connected, for sensing electric potentials of the heart tissue (myocardium) or for delivering electric signals, for example for delivering stimulation pulses to the surrounding heart tissue. FIG. 1 shows how the electrode poles, these being the tip electrode 22 and the annular electrode 24, are located in the apex of a right ventricle of a heart when the electrode line 20 is used.

Both the tip electrode 22 and the annular electrode 24 are electrically connected to a contact of a connector 28 at the proximal end of the electrode line 20 by way of at least one electric conductor 26. The connector 28 comprises electric contacts, which correspond to the electric contacts 16 of the contact bushing in the terminal housing 14 of the implantable cardiac stimulator. Connectors for electrode lines are standardized and referred to as IS-1 connectors or as IS-4 or DS-4 connector in accordance with the respective standard. Relevant standards are DIN 50077 and ISO 27186.

The electric conductors 26 in the electrode line 20 can be designed as approximately elongated sheathed cable conductors or helically coiled conductors. Such conductors, which electrically conductively connect functional electrode poles to electric contacts of the plug contact at the proximal end of the electrode line 20, are referred to as function conductors within the context of this specification, because they, for example, transmit electric signals used for treatment from the plug contact to the respective electrode pole, or conduct signals that represent sensed electric potentials from the respective electrode pole to the plug contact and thus serve the fundamental function of the medical device.

The electric conductors 26, which connect the electrode poles 22 or 24 to the electric contact of the connector 28 of the electrode line 20, are surrounded by an insulating jacket over the majority of the lengths thereof, so that an electric contact with the tissue of the heart is specifically established by the electrode poles.

In addition to the electrode poles 22 and 24, which are typically used for the (in this case ventricular) stimulation of the heart tissue, the electrode line 20 also comprises two larger-surface-area electrode poles 30 and 32, which serve as defibrillation electrodes and are formed by at least one exposed helically coiled wire.

It should be pointed out that this embodiment of the invention will be explained based on a right-ventricular cardiac pacemaker and defibrillator. A medical device within the meaning of one or more embodiments of the invention may be implemented with any ablation electrode line, for example, which in this case likewise projects into the heart of a patient and is controlled by a device located outside of the patient, and for this purpose is connected thereto.

Figure 2:
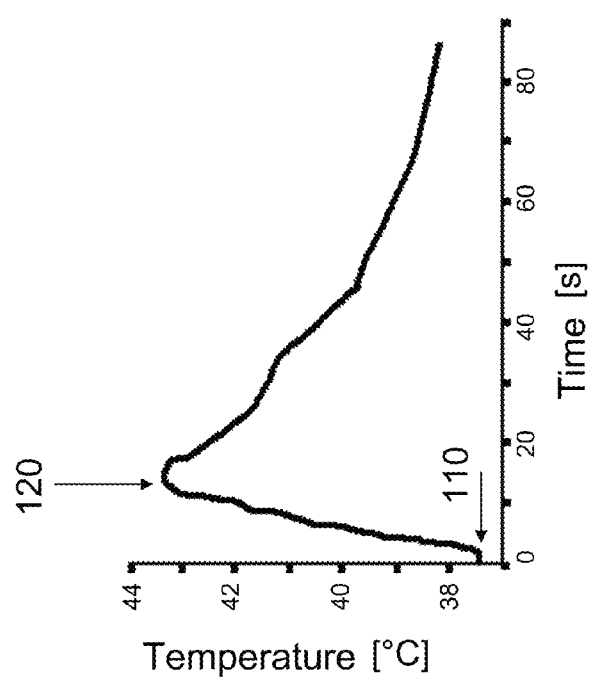
FIG. 2 shows, by way of example, a temperature curve on the electrode tip under the influence of radio-frequency alternating fields, as those which are present in a magnetic resonance tomograph (MRT).

FIG. 2 shows a typical temperature curve 100 of a conventional pacemaker/ICD electrode in a magnetic resonance tomograph (magnetic resonance imaging scanner, MRT). As the radio-frequency alternating field in the tomograph is switched on at the time 110, the temperature rises rapidly, wherein the gradient of the increase and the maximum achievable temperature are highly dependent on the electrode position in relation to the radio-frequency alternating fields of the MRT. When the radio-frequency alternating field is deactivated (at the time 120), the electrode tip cools off relatively quickly due to the comparatively low thermal capacity thereof.

FIGS. 3 to 8 each show different variants of a proximal end of an electrode line comprising an IS-1 or IS-4 connector.

Figure 3:
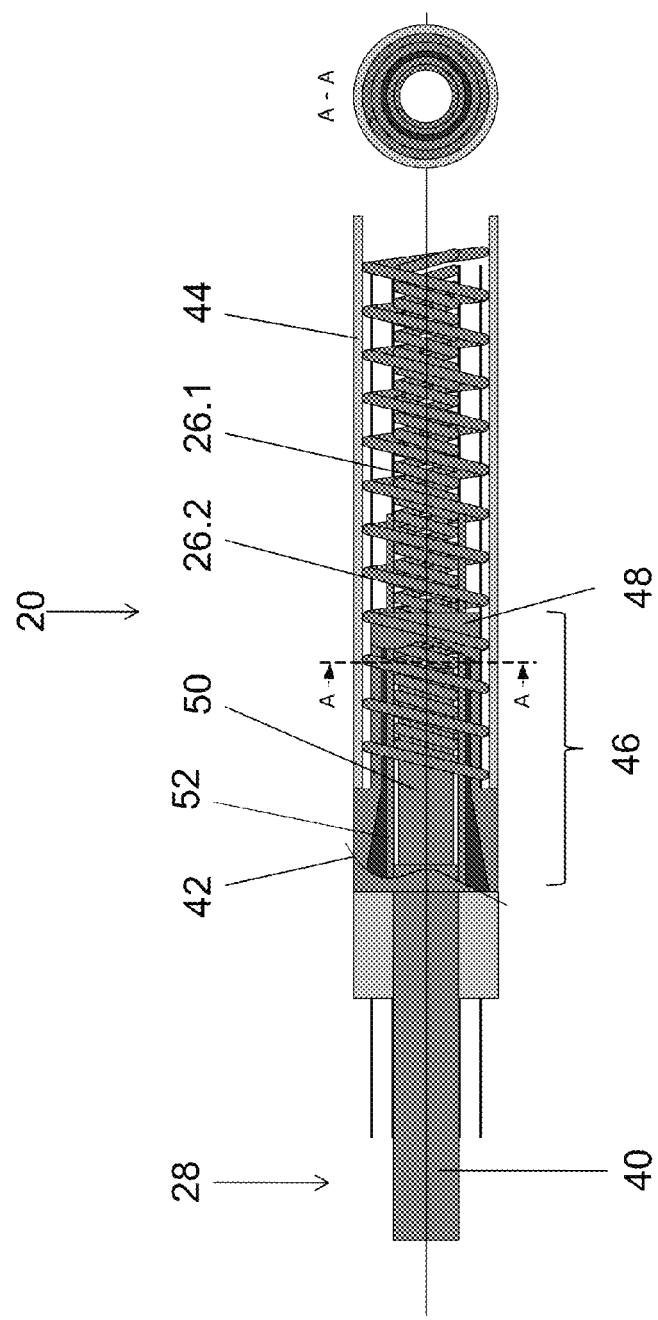
FIG. 3 shows a proximal end of an electrode line as the implantable medical device, which has a coaxial design comprising an IS-1 connector and in a transition region to the connector comprises a filling having adapted electromagnetic properties.

FIG. 3 shows the proximal end of an electrode line 20 comprising an IS-1 connector according to DIN 50077. The connector 28 comprises a first pin-shaped contact 40 and a second ring-shaped contact 42, which are insulated from each other. The pin-shaped contact 40 is electrically connected to a coiled inner conductor 26.1. The ring-shaped contact 42 is connected to a likewise coiled outer conductor 26.2. The inner conductor and outer conductor are both function conductors of the electrode line 20 and are surrounded by an insulating jacket 44. A distal section of the connector 28 connected to the inner conductor 26.1 and to the outer conductor 26.2 has a coaxial design and forms a transition region 46 from the connector 28 to the remaining electrode line 20.

In the transition region 46, the ring-shaped contact 42, including a connection section 48, surrounds the pin-shaped contact 40 and the connection section 50 thereof for connecting the inner conductor 26.1. A filling 52 is provided between the ring-shaped contact 42 in the outer connection section 48 and the pin-shaped contact 40 enclosed thereby with the inner connection section 50, with the electromagnetic and geometric properties of the filling being adjusted so as to continuously vary the characteristic impedance of the electrode line 20 in the transition region 46, thereby resulting in a substantially continuous adjustment of the characteristic impedance of the distal sections of the electrode line 20 and a characteristic impedance present proximally when the connector 28 is connected.

As is shown in FIG. 3, this adjustment of the characteristic impedance is achieved, among other things, by a geometry of the filling 52, wherein the volume of the filling increases in the region of the ring-shaped contact 42 in the proximal direction. The filling 52 has an insulating effect and is composed of a material described in more detail elsewhere and the impedance of the filling is suitable and lossy, whereby the filling 52 acts dissipatively.

Figure 4:
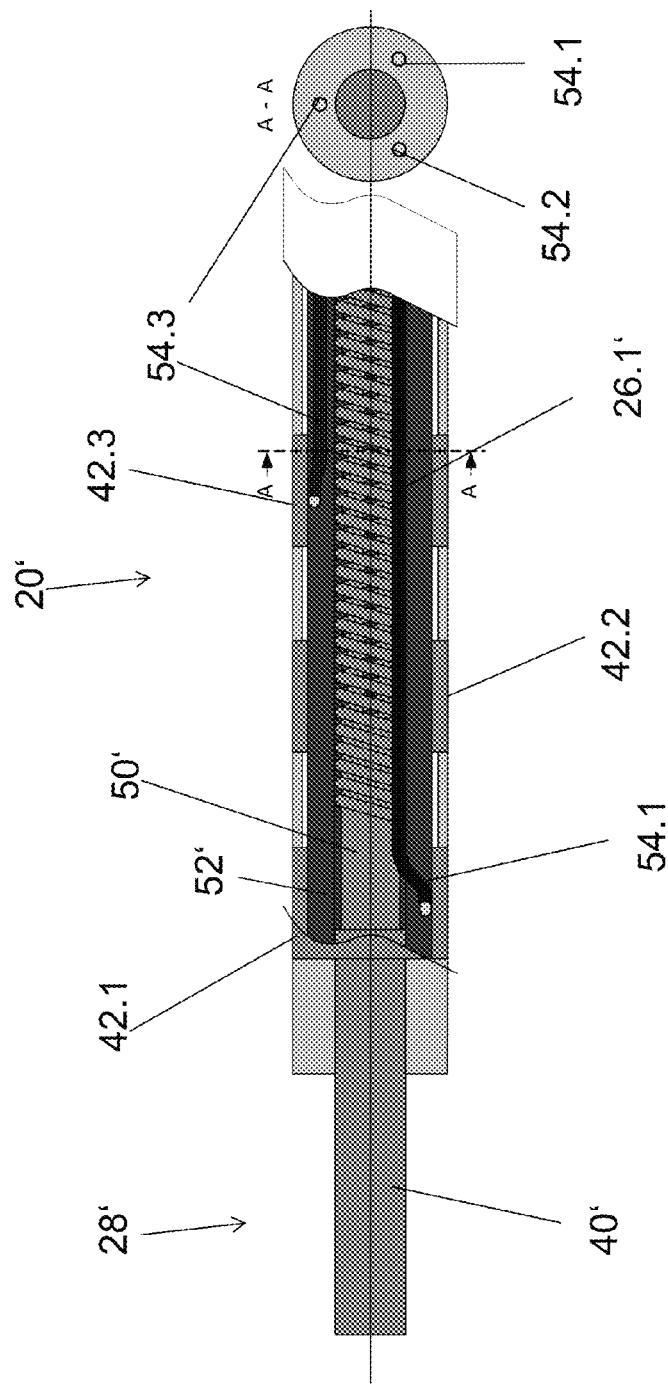
FIG. 4 shows a proximal end of an electrode line having a coaxial design and an IS-1 connector, the line having a change in the diameter ratio in a transition region to the connector.

FIG. 4 shows a proximal end section of an electrode line 20' comprising a connector 28', which is designed as an IS-4 connector according to ISO 27186. The connector comprises a pin-shaped contact 40' and a total of three ring-shaped contacts 42.1, 42.2 and 42.3. The pin-shaped contact 28' is connected to a coiled inner conductor 26.1' at the distal end. Each of the ring-shaped contacts 42.1, 42.2 and 42.3 is connected to a wire 54.1, 54.2 and 54.3 extending in the longitudinal direction of the electrode line 20. The wires 54.1, 54.2 and 54.3 represent outer conductors and are function conductors. A filling 52, which is composed of insulating material having adapted electromagnetic properties, is provided between the ring-shaped contacts 42.1, 42.2 and 42.3 and a distal connection section 50' of the pin-shaped contact 28 as well as the coiled inner conductor 26.1' connected thereto. Suitable materials and properties are described in more detail elsewhere in this specification.

Figure 5:
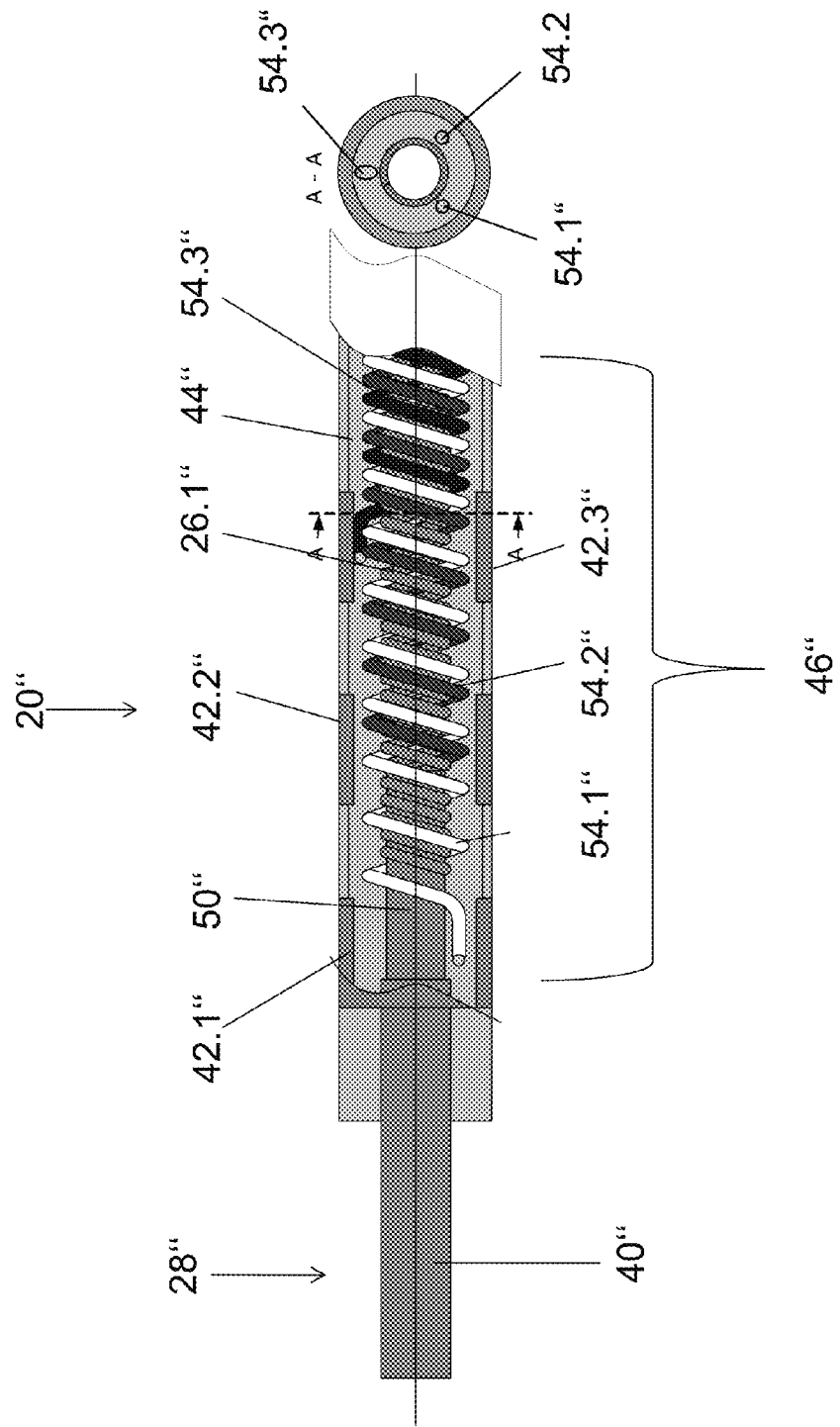
FIG. 5 shows a proximal end of an electrode line having a coaxial design and an IS-1 connector, the line having a change in the filling properties in the longitudinal direction of the transition region to the connector.

FIG. 5 shows a variant of an electrode line 20" comprising an IS-4 connector 28" similar to the arrangement in FIG. 4. Contrary to the variant of FIG. 4, the outer function conductors 54.1, 54.2 and 54.3 are coiled. The turn density of the coils forming the outer conductors 54.1', 54.2' and 54.3' can vary so that, in this way, a variation of the characteristic impedance is caused in the longitudinal direction of the transition region 42". In the variant shown in FIG. 5, a filling does not necessarily have to be provided in the space between the ring-shaped contacts 54.1", 54.2" and 54.3" and the inner connection section 50" of the pin-shaped plug contact 40", or the coiled inner conductors 26.1' connected thereto.

Figure 6:
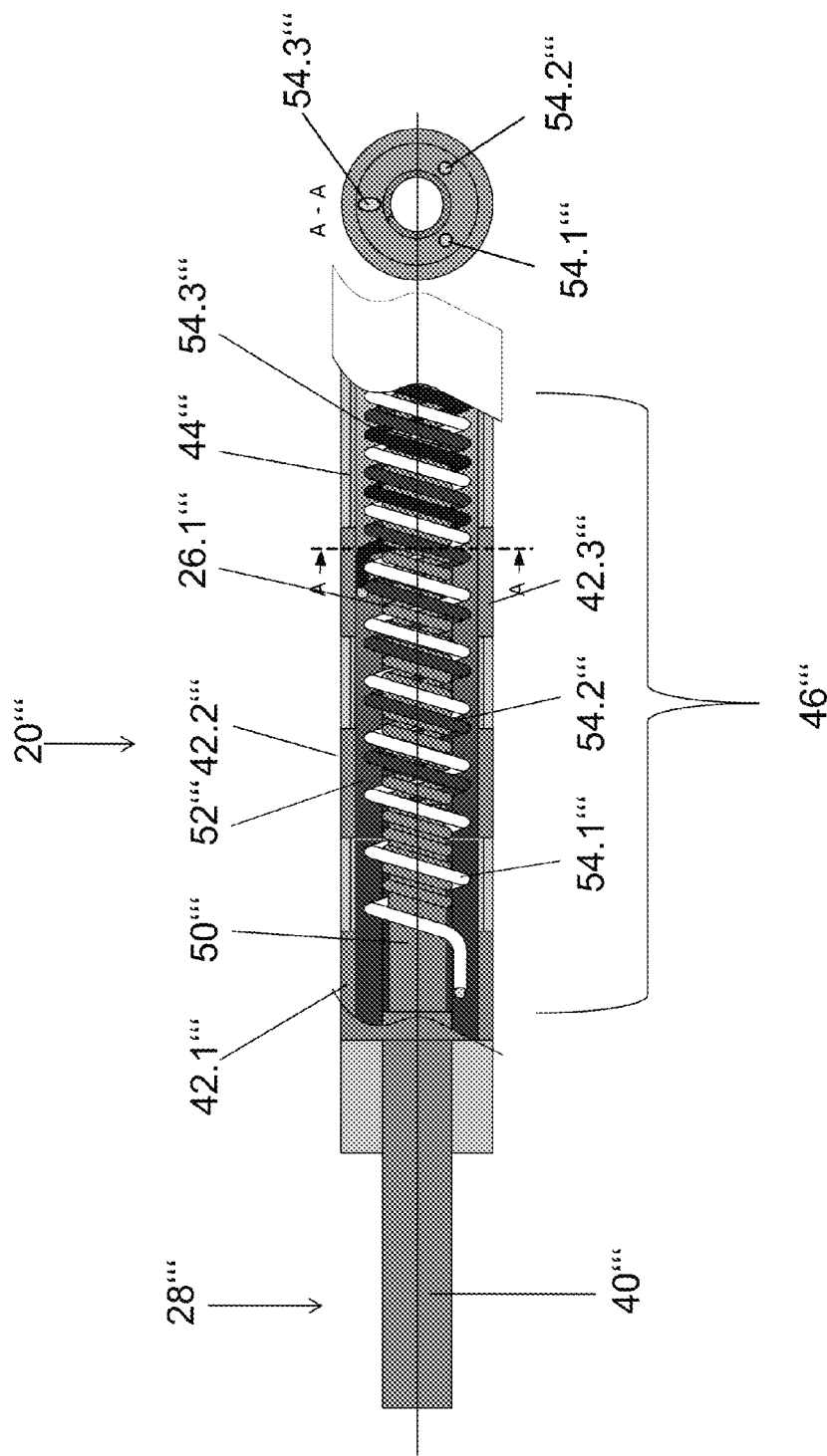
FIG. 6 shows a proximal end of an electrode line comprising an IS-4/DF-4 connector, wherein the line, in addition to a change in the filling properties in the longitudinal direction of the transition region to the connector, also has parallel wires and an inner coil.

In the variant shown in FIG. 6, the filling 52''' that is provided is such that the electromagnetic properties thereof vary in the longitudinal direction of the transition region 42''', so that a variation of the characteristic impedance is obtained and thus a substantially uniform adaptation of the characteristic impedance of the distal electrode line 20''' and of the characteristic impedance proximal of the connector 28'''. Except for the filling 42''', the variant according to FIG. 6 corresponds to the variant according to FIG. 5.

Figure 7:
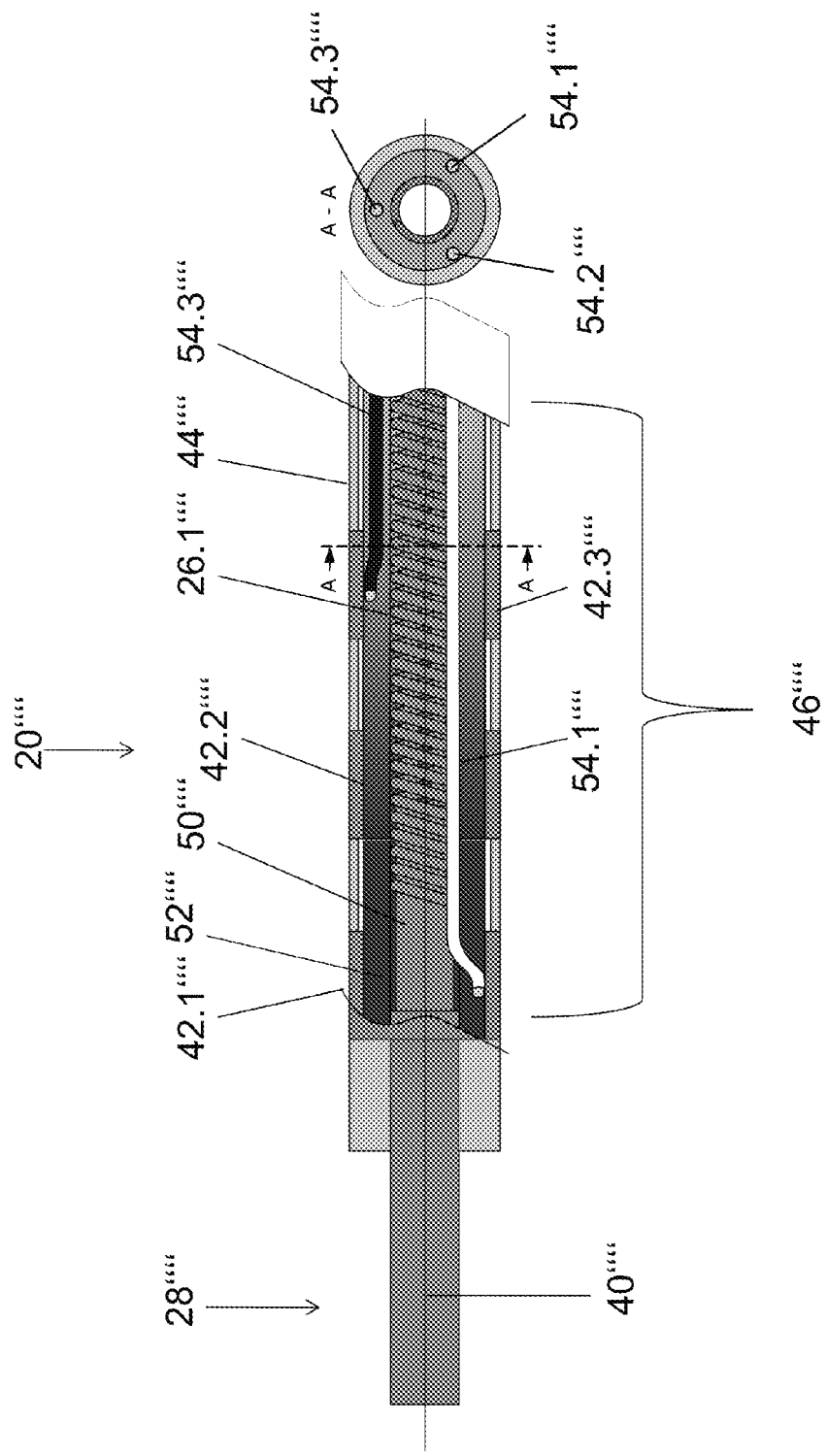
FIG. 7 shows a proximal end of an electrode line comprising an IS-4/DF-4 connector, the line having a change in the wire guidance. The wires can be twisted, for example, have variable gradients, or be combined with non-therapeutically used wires.

The same applies to the variant according to FIG. 7, which corresponds to the variant of FIG. 4, except for a filling 52''''. The filling 52'''' has varying electromagnetic properties in the longitudinal direction of the transition section 46'''', so that the characteristic impedance in this transition region also varies and a substantially inform transition is achieved between the characteristic impedance of the section of the electrode line 20 located distal of the transition section 46'''' and the characteristic impedance present proximal of the transition region 46'''' when the connector 28'''' is inserted in another device.

Figure 8:
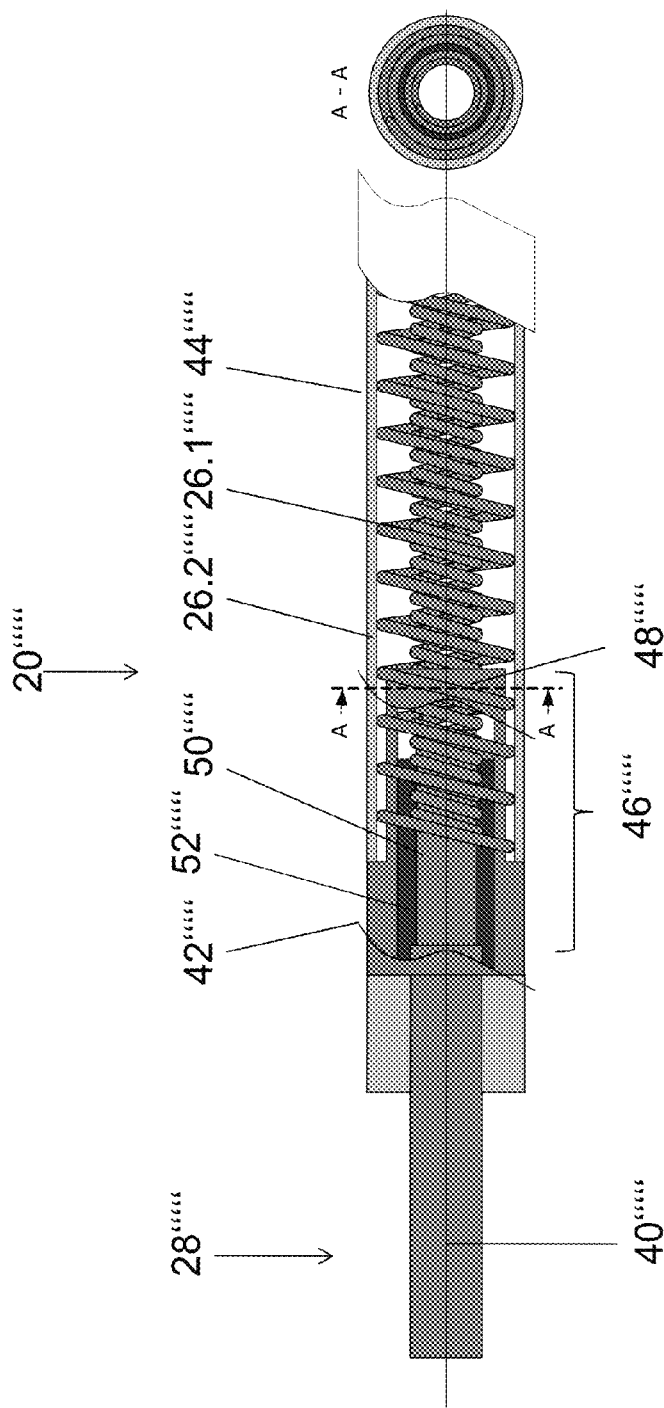
FIG. 8 shows a proximal end of an electrode line comprising an IS-4/DF-4 connector, the line having a change in the filling properties and in the wire guidance.

FIG. 8 shows a variant that is similar to the variant according to FIG. 3. The two variants differ with respect to the design of the filling 52. While in the variant according to FIG. 3 the geometry of the filling varies in the longitudinal direction of the transition region 46, in the variant according to FIG. 8 the electromagnetic properties of the filling vary in the longitudinal direction of the transition region 46''''.

As mentioned at the beginning, a material that meaningfully changes the characteristic impedance in the coaxial region should be used for the insulating filling 52 in the transition region to the connector. Based on such a change, the reflection and transmission factors will also vary in a range between $R_{S,W}[0;1]$ and $T_{S,W}[-1,1]$.

The factor is dependent on the difference of the characteristic impedances between the connector $Z_S$ and coil region $Z_W$.

In the embodiments, the respective transition region 46 is preferably designed to be low-reflecting and dissipative in the connector region. For this purpose, the characteristic impedance present there is adjusted to a level that is similarly high as in the adjoining line sections. Taking into consideration that the coaxial geometry changes, this must be done by way of the material properties.

Suitable materials for the respective filling 52 are fluoroplastics (PTFE, Teflon) and thermoplastic polycondensates (PEEK, PEKK), having a doping made of the following metals:
platinum & titanium
refractory materials: niobium, tantalum, palladium, tungsten.

Figure 9:
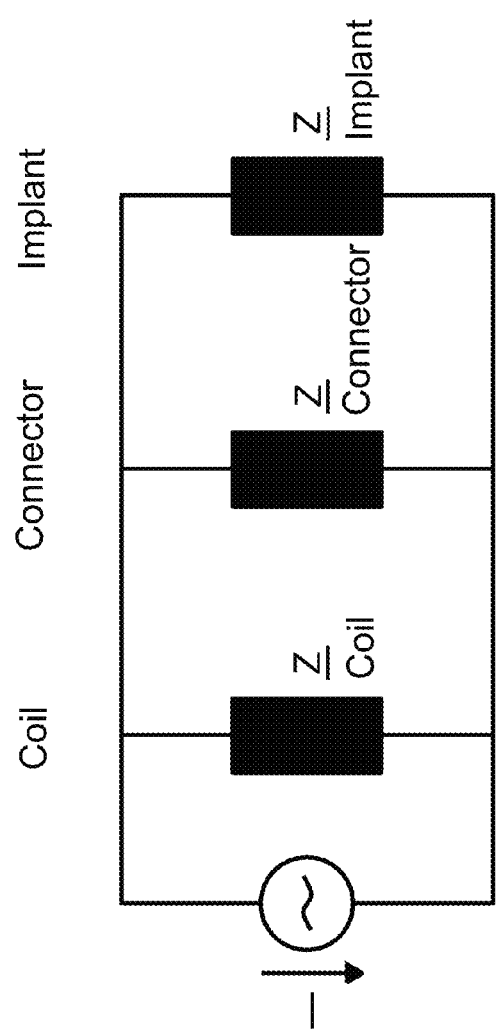
FIG. 9 shows an equivalent circuit for a network composed of characteristic impedances.

To illustrate the mechanism of action, FIG. 9 shows a network composed of characteristic impedances, as it was used for the calculations.

Figure 10:
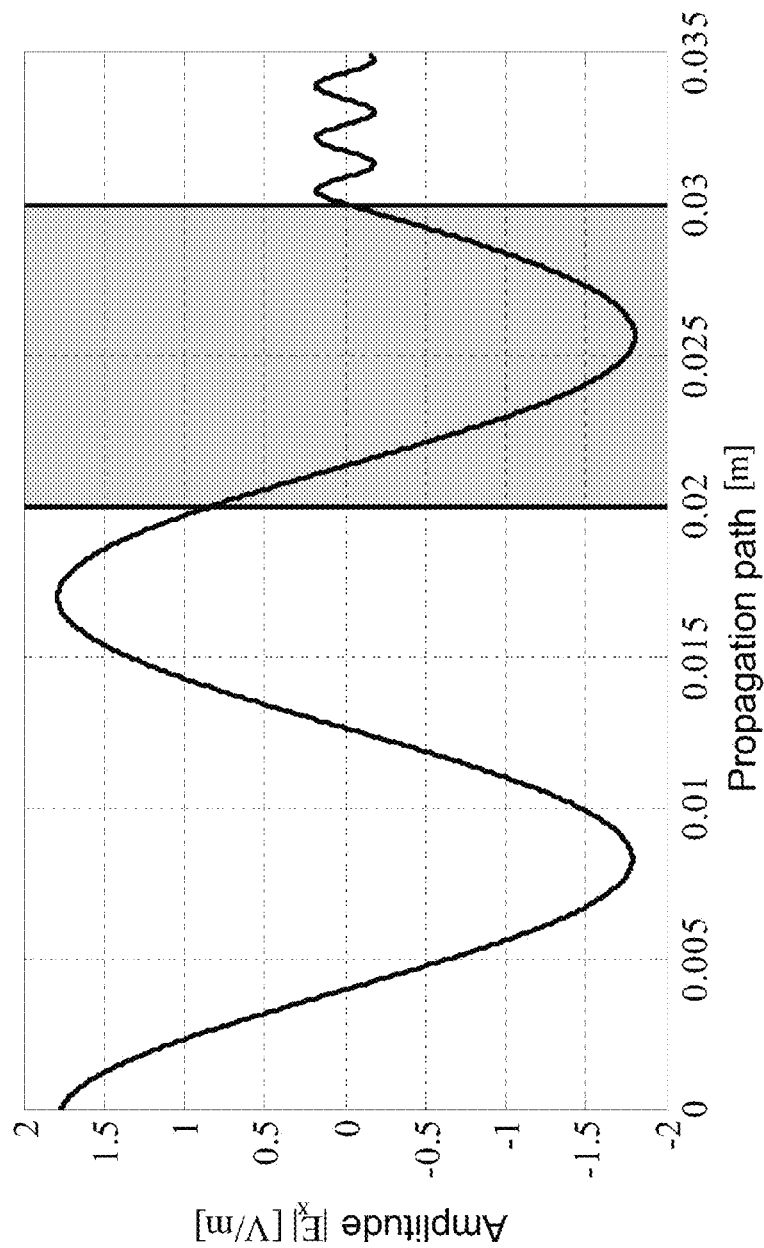
FIG. 10 shows the wave propagation on the interfaces without an attenuating connector, illustrated over the amplitude of the electric field coordinate; the input amplitude is adjusted to 1 V/m.
Figure 11:
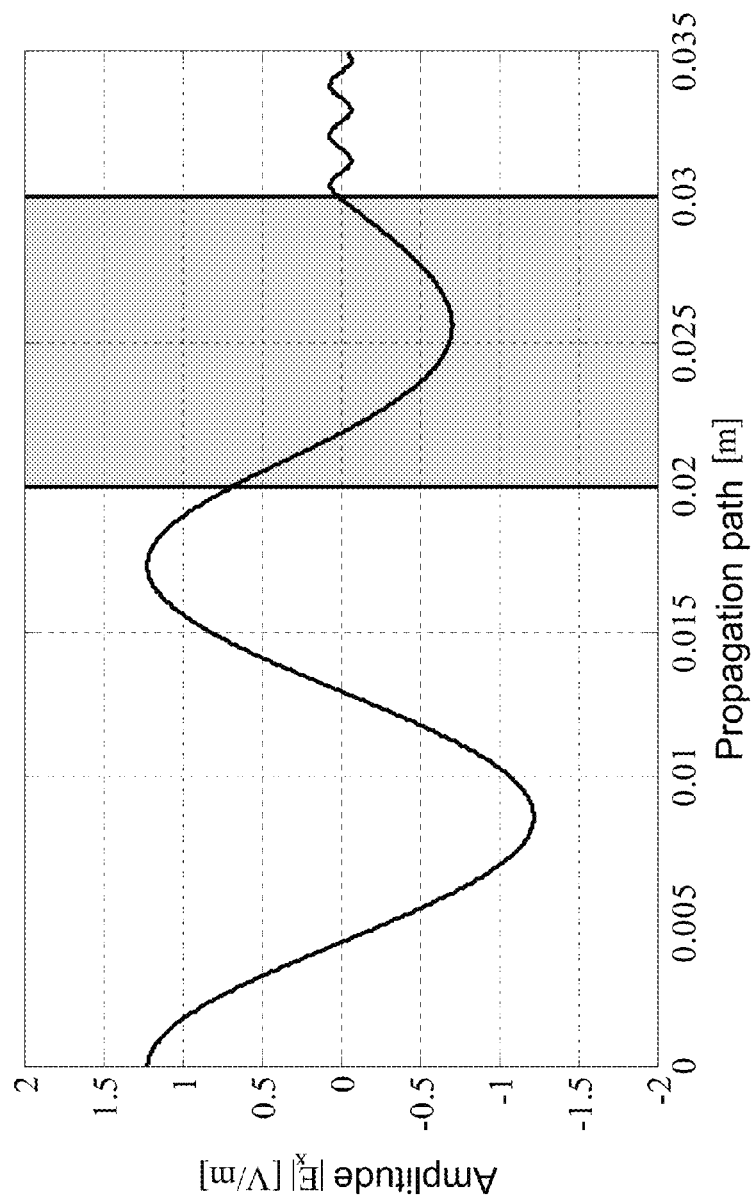
FIG. 11 shows the wave propagation on the interfaces with an attenuating connector, illustrated over the amplitude of the electric field coordinate; the input amplitude is adjusted to 1 V/m.

FIG. 10 shows the wave propagation on the interfaces without the attenuating connector, illustrated over the amplitude of the electric field coordinate, with the input amplitude adjusted to 1 V/m, and FIG. 11 shows the wave propagation on the interfaces with the attenuating connector, illustrated over the amplitude of the electric field coordinate, with the input amplitude adjusted to 1 V/m. FIG. 10 shows the behavior with strong reflection at the input of the implant without attenuation over the connector length. The resulting field strength in the coil region is almost twice as high as the input field strength. In FIG. 11, the connector region is designed to be dissipative. The resulting field strength is considerably lower in the coil region. The region shown in gray in FIG. 10 and FIG. 11 denotes the connector region, the white region to the left thereof denotes the coil region, and the region to the right of the gray region denotes the input of the IPG. The zero point on the abscissa denotes the start of the connector, and the electromagnetic wave propagates from left to right.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A device that can be temporarily introduced in a body or permanently implanted in the body, comprising:
at least one elongated electric function conductor configured to transmit treatment signals or diagnostic signals, or both, and further comprising a connector, which is connected to the at least one elongated electric function conductor and disposed on a proximal end of the at least one elongated electric function conductor, and configured to connect the device to a further device;
at least one further conductor;
wherein the at least one elongated electric function conductor and the at least one further conductor comprise an inner conductor and an outer conductor respectively, such that the outer conductor surrounds the inner conductor; and
wherein said at least one elongated electric function conductor and said at least one further conductor comprise a characteristic impedance between the at least one elongated electric function conductor and the at least one further conductor; and
a transition region from the at least one elongated electric function conductor to the connector that is configured such that said characteristic impedance between the at least one elongated electric function conductor and the at least one further conductor is configured to vary continuously through the transition region between a corresponding characteristic impedance of the device in a section located distal of the transition region and the characteristic impedance located proximal to the transition region when the connector is connected to said further device;
wherein the connector comprises a distal section, a pin-shaped contact and a ring-shaped contact, such that the pin-shaped contact electrically connects to the inner conductor, the ring-shaped contact electrically connects to the outer conductor, and the distal section connects to the inner conductor and the outer conductor forming the transition region;
wherein the transition region of the device comprises a filling, which alters the characteristic impedance and wherein properties and form of said filling are configured so that the desired characteristic impedance exists in the transition region; and
wherein a volume of the filling increases in the region of the ring-shaped contact in a direction towards the proximal end.

2. The implantable medical device according to claim 1, wherein the device is an electrode line configured to connect to an implantable medical device, wherein the electrode line comprises the connector at a proximal end and at least one electrode pole at a distal end, the at least one electrode pole being electrically connected to the connector by way of the at least one elongated electric function conductor.

3. The implantable medical device according to claim 1, wherein an impedance of the filling is configured to the characteristic impedance.

4. The implantable medical device according to claim 1, wherein the filling contains a material that is configured to act dissipatively at least in an operating frequency range of magnetic resonance tomographs.

5. The implantable medical device according to claim 4, wherein the material of the filling contains pyrolytic materials, doped plastic materials containing paraelectric, ferroelectric, diamagnetic, ferromagnetic, paramagnetic particles, or plastic materials with dielectric losses, or fluoroplastics and/or thermoplastic polycondensates, having a doping of one or more of the following metals:
platinum, titanium, and refractory metals such as: niobium, tantalum, palladium, and tungsten.

6. The implantable medical device according to claim 1, wherein the transition region comprises a coaxial structure.

7. The implantable medical device according to claim 1, wherein the filling is situated between said at least one elongated electric function conductor and said at least one further conductor.

8. The implantable medical device according to claim 1, wherein the filling is configured so that an impedance thereof changes in a longitudinal direction of the transition region.

9. The implantable medical device according to claim 1, wherein one or more of said at least one elongated electric function conductor is or are configured as one or more coils.

10. The implantable medical device according to claim 1, wherein one or more of said at least one elongated electric function conductor is or are configured as parallel wires.

11. The implantable medical device according to claim 9, wherein a turn density of said one or more coils is constant.

12. The implantable medical device according to claim 9, wherein the turn density of said one or more coils changes in a longitudinal direction of the transition region.

13. The implantable medical device according to claim 1, wherein in addition to the at least one elongated electric function conductor, said at least one further conductor is not used for said treatment signals or diagnostic signals, but rather is configured to minimize coupling of electromagnetic waves on the at least one elongated electric function conductor.

14. The implantable medical device according to claim 13, wherein the at least one further conductor is configured as a coil.

15. The implantable medical device according to claim 1, wherein the ring-shaped contact surrounds the pin-shaped contact in the transition region.

16. The implantable medical device according to claim 1, wherein the transition region comprises a first outer connection section and a second inner connection section, such that the filling is provided between the first outer connection section and the second inner connection section.

17. A device that can be temporarily introduced in a body or permanently implanted in the body, comprising:
at least one elongated electric function conductor configured to transmit treatment signals or diagnostic signals, or both, and further comprising a connector, which is connected to the at least one elongated electric function conductor and disposed on a proximal end of the at least one elongated electric function conductor, and configured to connect the device to a further device;
at least one further conductor;
wherein the at least one elongated electric function conductor and the at least one further conductor comprise an inner conductor and an outer conductor respectively, such that the outer conductor surrounds the inner conductor; and
wherein said at least one elongated electric function conductor and said at least one further conductor comprise a characteristic impedance between the at least one elongated electric function conductor and the at least one further conductor; and
a transition region from the at least one elongated electric function conductor to the connector that is configured such that said characteristic impedance between the at least one elongated electric function conductor and the at least one further conductor is configured to vary continuously through the transition region between a corresponding characteristic impedance of the device in a section located distal of the transition region and the characteristic impedance located proximal to the transition region when the connector is connected to said further device;
wherein the connector comprises a distal section, a pin-shaped contact and a ring-shaped contact, such that the pin-shaped contact electrically connects to the inner conductor, the ring-shaped contact electrically connects to the outer conductor, and the distal section connects to the inner conductor and the outer conductor forming the transition region,
wherein the ring-shaped contact surrounds the pin-shaped contact in the transition region,
wherein the transition region of the device comprises a filling, which alters the characteristic impedance and wherein properties and form of said filling are configured so that the desired characteristic impedance exists in the transition region, and
wherein the filling is configured so that an impedance thereof changes in a longitudinal direction of the transition region.

18. A device that can be temporarily introduced in a body or permanently implanted in the body, comprising:
at least one elongated electric function conductor configured to transmit treatment signals or diagnostic signals, or both, and further comprising a connector, which is connected to the at least one elongated electric function conductor and disposed on a proximal end of the at least one elongated electric function conductor, and configured to connect the device to a further device;
at least one further conductor;
wherein the at least one elongated electric function conductor and the at least one further conductor comprise an inner conductor and an outer conductor respectively, such that the outer conductor surrounds the inner conductor; and
wherein said at least one elongated electric function conductor and said at least one further conductor comprise a characteristic impedance between the at least one elongated electric function conductor and the at least one further conductor; and
a transition region from the at least one elongated electric function conductor to the connector that is configured such that said characteristic impedance between the at least one elongated electric function conductor and the at least one further conductor is configured to vary continuously through the transition region between a corresponding characteristic impedance of the device in a section located distal of the transition region and the characteristic impedance located proximal to the transition region when the connector is connected to said further device;
wherein the connector comprises a distal section, a pin-shaped contact and a ring-shaped contact, such that the pin-shaped contact electrically connects to the inner conductor, the ring-shaped contact electrically connects to the outer conductor, and the distal section connects to the inner conductor and the outer conductor forming the transition region,
wherein the transition region of the device comprises a filling, which alters the characteristic impedance and wherein properties and form of said filling are configured so that the desired characteristic impedance exists in the transition region, wherein said properties of the filling are configured to be adjusted to continuously vary the characteristic impedance of the filling in the transition region, and
wherein a volume of the filling increases in the region of the ring-shaped contact in a direction towards the proximal end.

\* \* \* \* \*